US00PP22158P2

(12) United States Plant Patent
Membrey et al.

(10) Patent No.: US PP22,158 P2
(45) Date of Patent: Sep. 20, 2011

(54) ***CUPHEA* PLANT NAMED 'SOUTHERN BORDER'**

(50) Latin Name: *Cuphea hyssopifolia*
Varietal Denomination: Southern Border

(76) Inventors: Stephen Membrey, Frankston (AU); Bryan Jackson, Dromana (AU)

( * ) Notice: Subject to any disclaimer, the term of this patent is extended or adjusted under 35 U.S.C. 154(b) by 0 days.

(21) Appl. No.: 12/799,850

(22) Filed: May 4, 2010

(51) Int. Cl.
*A01H 5/00* (2006.01)

(52) U.S. Cl. ..... Plt./420

(58) Field of Classification Search ..... Plt./420
See application file for complete search history.

*Primary Examiner* — June Hwu

(74) *Attorney, Agent, or Firm* — C. A. Whealy

(57) ABSTRACT

A new and distinct cultivar of *Cuphea* plant named 'Southern Border', characterized by its compact and mounding growth habit; freely branching habit; freely flowering habit; relatively large purple-colored flowers; and good garden performance.

2 Drawing Sheets

Botanical designation: *Cuphea hyssopifolia.*
Cultivar denomination: 'SOUTHERN BORDER'.

BACKGROUND OF THE INVENTION

The present invention relates to a new and distinct cultivar of *Cuphea* plant, botanically known as *Cuphea hyssopifolia* and hereinafter referred to by the name 'Southern Border'.

The new *Cuphea* plant is a product of a planned breeding program conducted by the Inventors in Dromana, Victoria, Australia. The objective of the breeding program is to create new compact *Cuphea* plants with numerous attractive flowers and good garden performance.

The new *Cuphea* plant originated from an open-pollination during the spring of 2002 in Dromana, Victoria, Australia of an unnamed seedling selection of *Cuphea hyssopifolia,* not patented, as the female, or seed, parent with an unknown selection of *Cuphea hyssopifolia* as the male, or pollen, parent. The new *Cuphea* plant was discovered and selected by the Inventors as a single flowering plant within the progeny of the stated open-pollination in a controlled greenhouse environment in Dromana, Victoria, Australia during the spring of 2003.

Asexual reproduction of the new *Cuphea* plant by cuttings in a controlled greenhouse environment in Dromana, Victoria, Australia since the spring of 2003, has shown that the unique features of this new *Cuphea* plant are stable and reproduced true to type in successive generations.

SUMMARY OF THE INVENTION

Plants of the new *Cuphea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Southern Border'. These characteristics in combination distinguish 'Southern Border' as a new and distinct cultivar of *Cuphea* plant:

1. Compact and mounding growth habit.
2. Freely branching habit.
3. Freely flowering habit.

4. Relatively large purple-colored flowers.
5. Good garden performance.

Plants of the new *Cuphea* can be compared to plants of the female parent selection. Plants of the new *Cuphea* differ from plants of the female parent selection in the following characteristics:

1. Plants of the new *Cuphea* are more mounding than and not as upright as plants of the female parent selection.
2. Plants of the new *Cuphea* are shorter than plants of the female parent selection.
3. Plants of the new *Cuphea* and the female parent selection differ in flower color as plants of the female parent selection have light red purple-colored flowers.

Plants of the new *Cuphea* can be compared to plants of the *Cuphea hyssopifolia* 'Magenta Border', disclosed in a U.S. Plant Patent application filed concurrently. In side-by-side comparisons conducted in Cranbourne, Victoria, Australia, plants of the new *Cuphea* differed from plants of 'Magenta Border' in the following characteristics:

1. Plants of the new *Cuphea* were larger than plants of 'Magenta Border'.
2. Plants of the new *Cuphea* were faster growing than plants of 'Magenta Border'.
3. Plants of the new *Cuphea* and 'Magenta Border' differed in flower color as plants of 'Magenta Border' had red purple-colored flowers.

Plants of the new *Cuphea* can also be compared to plants of the *Cuphea hyssopifolia* 'Rob's Mauve', not patented. In side-by-side comparisons conducted in Cranbourne, Victoria, Australia, plants of the new *Cuphea* differed from plants of 'Rob's Mauve' in the following characteristics:

1. Plants of the new *Cuphea* were more mounding than and not as upright as plants of 'Rob's Mauve'.
2. Plants of the new *Cuphea* were more compact than plants of 'Rob's Mauve'.
3. Plants of the new *Cuphea* were more freely branching than plants of 'Rob's Mauve'.
4. Plants of the new *Cuphea* were more freely flowering than plants of 'Rob's Mauve'.

5. Plants of the new *Cuphea* and 'Rob's Mauve' differed in flower color as plants of 'Rob's Mauve' had darker purple-colored flowers.

BRIEF DESCRIPTION OF THE PHOTOGRAPHS

The accompanying colored photographs illustrate the overall appearance of the new *Cuphea* plant showing the colors as true as it is reasonably possible to obtain in colored reproductions of this type. Colors in the photographs may differ slightly from the color values cited in the detailed botanical description which accurately describe the colors of the new *Cuphea* plant.

The photograph on the first sheet comprises a side perspective view of a typical flowering plant of 'Southern Border' grown in a container.

The photograph on the second sheet is a close-up view of a typical flowering plant of 'Southern Border'.

DETAILED BOTANICAL DESCRIPTION

The aforementioned photographs and following observations, measurements and values describe plants grown during the summer and autumn in 15-cm containers in a polyethylene-covered greenhouse in Cranbourne, Victoria, Australia and under cultural conditions which approximate commercial *Cuphea* plant production. During the production of the plants, day temperatures ranged from 12° C. to 40° C., night temperatures ranged from 6° C. to 28° C. and light levels ranged from 1,000 to 9,000 foot-candles. Rooted young plants were pinched one time and were four months old when the photographs and description were taken. In the following description, color references are made to The Royal Horticultural Society Colour Chart, 1995 Edition, except where general terms of ordinary dictionary significance are used.

Botanical classification: *Cuphea hyssopifolia* 'Southern Border'.

Parentage:

*Female, or seed, parent.*—Unnamed seedling selection of *Cuphea hyssopifolia,* not patented.

*Male, or pollen, parent.*—Unknown selection of *Cuphea hyssopifolia,* not patented.

Propagation:

*Type.*—By cuttings.

*Time to initiate roots, summer.*—About 12 to 18 days at 22° C. to 30° C.

*Time to initiate roots, winter.*—About 18 to 25 days at 10° C. to 15° C.

*Time to produce a rooted young plant, summer.*—About 20 to 30 days at 16° C. to 39° C.

*Time to produce a rooted young plant, winter.*—About 25 to 45 days at 10° C. to 15° C.

*Root description.*—Fine, fibrous; white in color.

*Rooting habit.*—Freely branching; dense.

Plant description:

*Plant and growth habit.*—Herbaceous annual; compact and mounding growth habit; freely branching habit; moderately vigorous to vigorous growth habit.

*Plant height.*—About 15 cm to 20 cm.

*Plant diameter.*—About 20 cm to 25 cm.

Lateral branch description:

*Length.*—About 4 cm to 9 cm.

*Diameter.*—About 2 mm.

*Internode length.*—About 0.2 cm to 7 cm.

*Aspect.*—About 60° to 90° from vertical.

*Texture.*—Sparsely pubescent.

*Color, young stems.*—Close to 174B.

*Color, developed stems.*—Close to 152A.

Foliage description:

*Arrangement.*—Opposite, occasionally alternate; simple.

*Length.*—About 1.4 cm to 3.1 cm.

*Width.*—About 3 mm to 5 mm.

*Shape.*—Oblong to broadly lanceolate.

*Apex.*—Bluntly acute.

*Base.*—Blunt.

*Margin.*—Entire; slightly recurved.

*Texture, upper and lower surfaces.*—Smooth, glabrous.

*Venation pattern.*—Pinnate.

*Color.*—Developing leaves, upper and lower surfaces: Close to 144A to 144B. Fully developed leaves, upper surface: Close to 146A; venation, close to 138B. Fully developed leaves, lower surface: Close to 146B; venation, close to 138B.

*Petiole length.*—About 1 mm.

*Petiole diameter.*—About 1 mm.

*Petiole texture, upper surface.*—Pubescent.

*Petiole texture, lower surface.*—Smooth, glabrous.

*Petiole color, upper and lower surfaces.*—Close to 138B.

Flower description:

*Flower arrangement and habit.*—Single tubular flowers with flaring petals; flowers arising from leaf axils; freely flowering habit with about four to eight flowers and flower buds per lateral stem; flowers face upright to outwardly.

*Fragrance.*—None detected.

*Natural flowering season.*—Plants flower continuously from the spring through the fall in Victoria, Australia; plants begin flowering about six to nine weeks after planting.

*Flower longevity.*—Individual flowers last about six to ten days on the plant; flowers not persistent.

*Flower diameter.*—About 9 mm to 11 mm.

*Flower length.*—About 9 mm to 11 mm.

*Flower bud.*—Shape: Cylindrical. Length: About 4 mm to 5 mm. Diameter: About 1 mm to 1.5 mm. Color: Close to 145A; towards the apex, close to 145D.

*Petals.*—Arrangement: Five to six petals arranged in a single whorl. Length: About 4 mm to 5 mm. Width: About 2 mm to 4 mm. Shape: Broadly elliptic. Apex: Bluntly acute. Base: Broadly tapering. Margin: Entire. Texture, upper and lower surfaces: Smooth, glabrous; crinkled. Color: When opening, upper and lower surfaces: Close to 74A. Fully opened, upper surface: Close to 78B; with development, color becoming closer to 78D. Fully opened, lower surface: Close to 78B; with development, color becoming closer to 78B to 78C. Flower tube: Close to 155D. Flower throat: Close to 154D.

*Sepals.*—Arrangement: Six to seven sepals fused in a single whorl; calyx, narrowly campanulate. Length: About 1 mm. Width: About 1 mm. Shape: Triangular. Apex: Shortly pointed. Base: Obtuse. Margin: Entire. Texture, upper and lower surfaces: Smooth, glabrous. Color, upper and lower surfaces: Close to 146B; towards the apex, close to 183B.

*Peduncles.*—Length: About 4 mm. Diameter: About 0.5 mm. Angle: About 60° from stem axis. Strength: Fairly weak. Texture: Slightly pubescent. Color: Close to 145A; towards the apex, close to 186A.

*Reproductive organs.*—Stamens: Quantity per flower: About eleven. Pollen amount: Scarce. Pollen color: Close to 4D. Pistils: Quantity: One per flower. Pistil length: About 8 mm. Style length: About 6 mm. Style color: Close to 155D; towards the apex, close to 78D. Stigma color: Close to 155C. Ovary color: Close to 155A to 155D.

*Seeds.*—Quantity: Numerous seeds are produced.

Garden performance: Plants of the new *Cuphea* have been observed to have good garden performance and tolerate wind, rain and to tolerate temperatures ranging from −1° C. to 45° C.

Pathogen/pest resistance: Plants of the new *Cuphea* have not been observed to be resistant to pathogens and pests common to *Cuphea* plants.

It is claimed:

1. A new and distinct *Cuphea* plant named 'Southern Border' as illustrated and described.

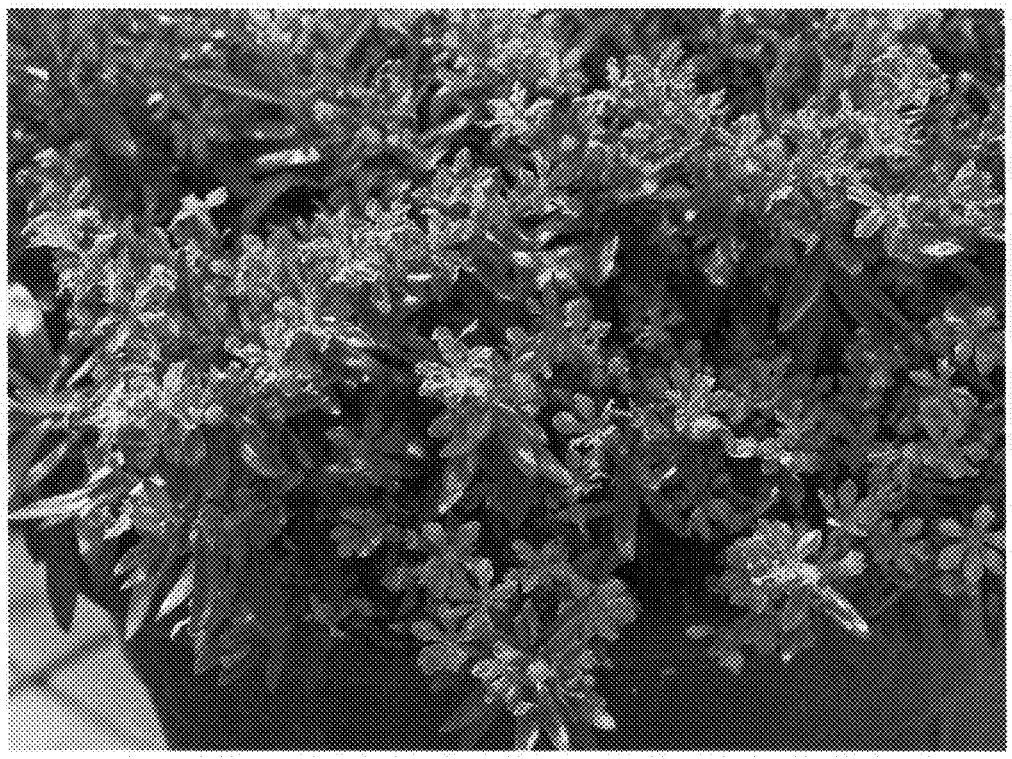

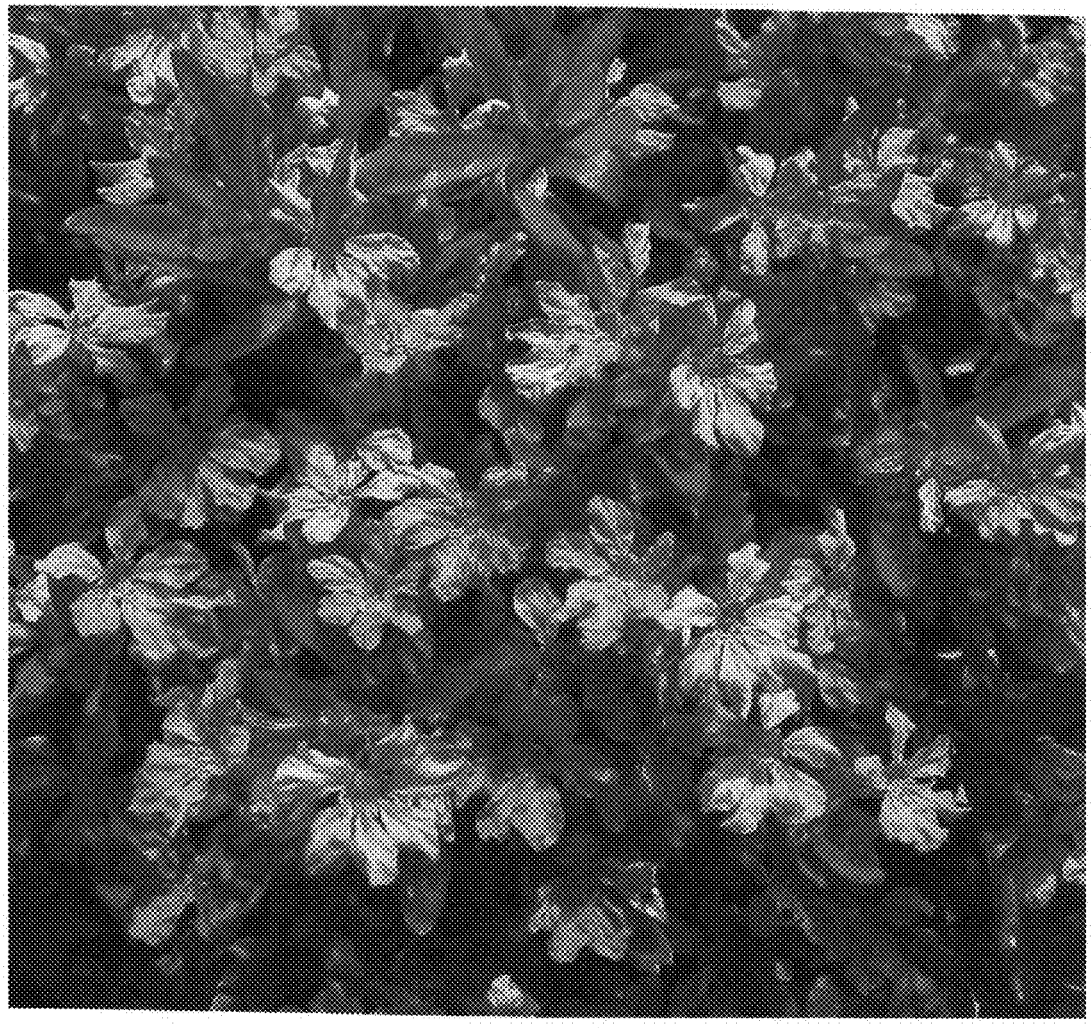

* * * * *